United States Patent
Carrino et al.

(10) Patent No.: US 6,294,326 B1
(45) Date of Patent: *Sep. 25, 2001

(54) ANALYTE DETECTION PROCESS USING DUAL LABELED PROBES

(75) Inventors: John J. Carrino, San Diego, CA (US); John R. Ertl; John A. Salituro, both of Racine, WI (US); Paul M. Jung, Chicago, IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/966,341

(22) Filed: Nov. 7, 1997

(51) Int. Cl.$^7$ .......................... C07H 21/02; C07H 21/04; C07H 21/00
(52) U.S. Cl. .............. 435/6; 435/91.1; 435/91.2; 435/183; 436/94; 536/23.1; 536/24.3; 536/24.33; 536/25.3; 536/25.31
(58) Field of Search .............................. 435/6, 91.1, 91.2, 435/183; 436/94; 536/23.1, 24.3, 24.33, 25.3, 25.31

(56) References Cited

U.S. PATENT DOCUMENTS

| 4,683,195 | 7/1987 | Mullis et al. . |
|---|---|---|
| 4,683,202 | 7/1987 | Mullis . |
| 5,210,015 | 5/1993 | Gelfand et al. . |
| 5,322,770 | 6/1994 | Gelfand . |
| 5,424,414 | 6/1995 | Mattingly . |
| 5,464,746 | 11/1995 | Fino . |
| 5,538,848 | 7/1996 | Livak et al. . |
| 5,573,907 | 11/1996 | Carrino et al. . |

FOREIGN PATENT DOCUMENTS

| 9202638 | 2/1992 | (WO) ............................... C12Q/1/68 |
|---|---|---|
| 9619731 | 6/1996 | (WO) ........................... G01N/33/354 |
| 9729210 | 8/1997 | (WO) ............................... C12Q/1/68 |

OTHER PUBLICATIONS

Edwards et al. Multiplex PCR: advantages, development, and applications, PCR Methods and Applications, S65–S75, 1994.*

Heid, C. A., et al., "Real Time Quantitative PCR", *Genome Research*, 6(10):986–994 (1996).

* cited by examiner

*Primary Examiner*—Eggerton A. Campbell
*Assistant Examiner*—Joyce Tung
(74) *Attorney, Agent, or Firm*—Paul D. Yasger

(57) ABSTRACT

Provided herein is a method for detecting the presence of a target nucleic acid sequence in a sample. The present method uses a combination of dual labeled probes and heterogeneous detection methods.

14 Claims, 2 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 190 bases
       (B) TYPE: nucleic acid
       (C) STRANDEDNESS: single
       (D) TOPOLOGY: linear (ii) MOLECULE TYPE: genomic RNA (HIV-1/SF-2)

(xi) SEQUENCE DESCRIPTION: SEQ ID NO:1:

ATCAGAAGGA GCCACCCCAC AAGATTTAAA CACCATGCTA AACACAGTGG          50

GGGGACATCA AGCAGCCATG CAAATGTTAA AAGAGACTAT CAATGAGGAA         100

GCTGCAGAAT GGGATAGAGT GCATCCAGTG CATGCAGGGC CTATTGCACC         150

AGGCCAAATG AGAGAACCAA GGGGAAGTGA CATAGCAGGA                    190

(2) INFORMATION FOR SEQ ID NO:2:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: synthetic DNA (xi) SEQUENCE DESCRIPTION: SEQ ID NO:2:

AAGGAGCCAC CCCACAAGAT TTAAAC                                    26

(2) INFORMATION FOR SEQ ID NO:3:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: synthetic DNA (xi) SEQUENCE DESCRIPTION: SEQ ID NO:3:

TGCTATGTCA CTTCCCCTTG GTTCTCT                                   27

(2) INFORMATION FOR SEQ ID NO: 4:

(i) SEQUENCE CHARACTERISTICS:
       (A) LENGTH: 28
       (B) TYPE:  nucleic acid
       (C) STRANDEDNESS:  single
       (D) TOPOLOGY:  linear (ii) MOLECULE TYPE: synthetic DNA (xi) SEQUENCE DESCRIPTION: SEQ ID NO: 4:

GCTAAACACA GTGGGGGGAC ATCAAGCA                                  28

(2) INFORMATION FOR SEQ ID NO:5:

(i) SEQUENCE CHARACTERISTICS:
       (A) LENGTH: 38 base pairs
       (B) TYPE: nucleic acid (C) STRANDEDNESS: single
            (D) TOPOLOGY: linear (ii) MOLECULE TYPE: synthetic DNA (xi) SEQUENCE DESCRIPTION: SEQ ID NO:5:

CGTCATCCAG TGCATGCAGG GCCTATTGCA CCAGGCCA                                38

(2) INFORMATION FOR SEQ ID NO:6:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:6:

TAATGGCCTG GTGCAATAGG CCCTGCATGC ACTGGATG                                38

(2) INFORMATION FOR SEQ ID NO:7:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: synthetic DNA (xi) SEQUENCE DESCRIPTION: SEQ ID NO:7:

AATTGCTAAA CACAGTGGGG GGACATCAAG CAGCCATGCA                              40

(2) INFORMATION FOR SEQ ID NO:8:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: synthetic DNA (xi) SEQUENCE DESCRIPTION: SEQ ID NO:8:

ATTGCAGGAA GCCGTCTTCC CTCACAGGGT GCCC                                   34

(2) INFORMATION FOR SEQ ID NO:9:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: synthetic DNA (xi) SEQUENCE DESCRIPTION: SEQ ID NO:9:

TCTGGGCACC CTGTGAGGGA AGACGGCTTC CTGC                                   34

(2) INFORMATION FOR SEQ ID NO:10:

(i) SEQUENCE CHARACTERISTICS:
            (A) LENGTH: 227 base pairs
            (B) TYPE: nucleic acid
            (C) STRANDEDNESS: single
            (D) TOPOLOGY: linear (ii) MOLECULE TYPE: genomic DNA -continued

```
(xi) SEQUENCE DESCRIPTION: SEQ ID NO:10:

CGCGGATCCG CTAAACACAG TGGGGGGACA TCAAGCATTG AGTCCATGGG            50

GAGCTTTGAG ATTGCTGTGA GAGAGATGTA GTTGTAGATT TGATTCTGGA           100

CCATGGCAGT AGATGGTTTC TTGGGCATCA GCTGGTTTAC ATACTCTGGA           150

GCAGGCAGGA AGCCGTCTTC CCTCACAGGG TGCCCCCCAT TAGAGAACCA           200

AGGGGAACTG ACATAGCAGA ATTCCGG                                    227
```

ANALYTE DETECTION PROCESS USING DUAL LABELED PROBES

TECHNICAL FIELD OF THE INVENTION

The field of this invention is analyte detection. More particularly, the present invention relates to the detection of target nucleic acids in a test sample using a dual labeled oligonucleotide probe and heterogeneous detection methods.

BACKGROUND OF THE INVENTION

There are a number of methods for detecting the presence of a particular nucleic acid molecule in a sample. By way of example, detecting amplification products from the polymerase chain reaction (PCR), ligase chain reaction (LCR), gap ligase chain reaction (GLCR), Qβ replicase, self-sustained sequence replication and strand displacement amplification (SDA), as a means for detecting a particular nucleic acid sequence, have all been described (See, e.g., Roche Molecular Systems, Inc., *Current Opinion in Biotechnology* 4:41–47, 1993). These amplification processes are becoming useful clinical diagnostic tools to, for example, construct assays which detect infectious organisms in a test sample. Additionally, amplification assays have been used in research and development fields as well as in forensic fields to, for example, detect genetic defects.

LCR described in European Patent Application EP-A-320-308; PCR and a variation of PCR known as reverse transcription PCR (RT-PCR) described in U.S. Pat. Nos. 4,683,202, 4,683,195, and 5,322,770 (the disclosures of which are incorporated herein by reference); and GLCR described in U.S. Pat. No. 5,427,930 (the disclosure of which is also incorporated herein by reference) are widely used in nucleic acid amplification based assays designed to detect a target sequence and therefore the organism which is associated with the target sequence. These amplification techniques typically employ primers or probes to repeatedly generate copies of a target nucleic acid sequence, which is usually a small region of a much larger nucleic acid sequence. Primers and probes are themselves nucleic acid sequences that are complementary to regions of a target sequence and under suitable conditions, hybridize or bind to the complementary portions of the target sequence. Copies of the target sequence are typically generated by the process of primer or probe extension that utilizes enzymes such as polymerase or ligase, separately or in combination, to add nucleotides (or probes) to the hybridized primers or probes. The nucleotides (or probes) that are added to the primers or probes are also complementary to the target sequence. Once the primers or probes have been sufficiently extended and/or ligated they are separated from the target sequence and a sequence complementary to the target sequence is formed. A new round of extension can then take place to amplify the number of complementary target sequences. Additionally, the sequences that are complementary to the target sequence can serve as templates for primer or probe extension to thereby amplify the number of target sequences. Hence multiple copies of the target sequence and its complementary sequence are produced.

The presence or amount of amplified target sequences and/or sequences complementary to the target sequence in a solution can be detected in a number of ways. Typically, the amplified sequences are detected using labeled primers that are incorporated into the amplified sequences, labeled probes that hybridize to the amplification products or a combination of both. For example, a sandwich assay format (variously referred to as a heterogeneous assay format) can be employed to detect the presence or amount of amplified nucleic acid sequences in a solution. Specifically, amplified sequences can be immobilized on a solid phase such as a suspension of microparticles coated with a capturing moiety. That capturing moiety binds to, for example, a capture hapten incorporated into the amplified sequences. Accordingly, when the sequences are contacted with the capture reagent, the sequences become immobilized on the solid support. A second hapten, also incorporated into the amplified sequences, can be used to detect the sequences immobilized to the solid support. In particular, the support bound sequences can be contacted with a conjugate comprising, for example, a fluorescent moiety conjugated to a member that specifically binds the second hapten. Thus, the fluorescent moiety also is immobilized to the solid phase by virtue of the second hapten and the fluorescent moiety can then be detected as an indication of the amplified sequences on the solid support.

More recently, homogeneous methods for detecting amplified sequences have been described. The so-called "Taq-Man" method, which is described in U.S. Pat. Nos. 5,210,015 and 5,538,848, the disclosures of which are incorporated herein by reference, is one such method. Briefly, the method uses a labeled oligonucleotide probe that specifically anneals to the target nucleic acid at a position downstream from a primer sequence (i.e., in the direction of primer extension). The probe contains both a reporter fluorescent molecule and a quencher molecule positioned on the probe such that the quencher molecule inhibits the detection of the fluorescent signal when the probe is intact. As amplification occurs (only in the presence of the target), the primer is extended by the action of a DNA polymerase and the probe is digested by the exonuclease activity of the polymerase. Upon such digestion of the probe, the quencher molecule is physically separated from the reporter molecule to enable detection of the fluorescent signal. In this manner, fluorescence increases with amplification and indicates the presence of the target sequence.

Unfortunately, however, there is no method for detecting amplified nucleic acid sequences using heterogeneous techniques such that the signal detected is imminently coupled to the amplification of the target sequence.

BRIEF SUMMARY OF THE INVENTION

The present invention provides a method for detecting the presence of a target sequence in a test sample. The process includes the steps of: (a) forming a reaction mixture comprising the test sample and any target sequence that may be contained therein, amplification reagents, and a primer and probe that hybridize to the same strand of the target sequence such that the probe is downstream from the primer; (b) degrading the probe in the reaction mixture to separate a first and a second label present on the intact probe where the first label is a specific binding member; (c) contacting the reaction mixture with a capture reagent to form a first specific-binding-member/capture reagent complex; and (d) detecting the second label associated with the first specific-binding-member/capture reagent complex, wherein a loss of signal indicates the presence of the target sequence. The reaction mixture can further include probe and/or primer sequences that hybridize to target sequence's complementary sequence. Additionally, the reaction may include additional probe and/or primer sequences that hybridize to another one or more target sequences to enable detection of multiple target sequences.

The second label on the probe can be a directly detectable label or it also may be a second specific binding member. In cases where the second label is a specific binding member, the method can further include the step of contacting the first specific-binding-member/capture reagent complex with a conjugate to detect the second label. The method can further include single or multiple wash steps that can be performed, for example, (i) after forming the first specific-binding-member/capture reagent complex and prior to contacting the so-formed complexes with a conjugate or detecting the second label, and/or (ii) after contacting the first specific-binding-member/capture reagent complex with the conjugate and prior to detecting the second label.

In one embodiment, the probe is degraded by including an enzyme having polymerase and 5'→3' exonuclease activity in the reaction mixture. According to this embodiment, the target sequence is concomitantly amplified as the probe is degraded. In another embodiment, the probe is degraded by including an enzyme with polymerase and 5'→3' exonuclease activity in the reaction mixture but the degradation of the probe can be stopped at a predetermined point such that the extended primer and the remaining probe are ligation competent. According to this embodiment, the target can be amplified by ligating the ligation competent primer and probe by, for example, including an enzyme having ligase activity in the reaction mixture. According to embodiments where the target sequence is amplified, the number of target sequence copies can be increased by cycling alternate hybridization and dissociation conditions such as by thermal cycling the reaction mixture.

BRIEF DESCRIPTION OF THE DRAWINGS

In the drawings, which form a portion of the specification.

DETAILED DESCRIPTION OF THE INVENTION

Figure 1A:
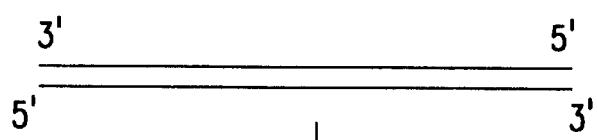
FIGS. 1(A)–(E) show an embodiment of the present invention.

The phrase "amplification reaction reagents" as used herein means reagents which are well known for their use in nucleic acid amplification reactions and may include but are not limited to: a single or multiple reagent, reagents, enzyme or enzymes separately or individually having 5'→3' exonuclease, reverse transcriptase, polymerase, and/or ligase activity; enzyme cofactors such as magnesium; salts; nicotinamide adenine dinucleotide (NAD); and deoxynucleoside triphosphates (dNTPs) such as, for example, deoxyadenosine triphosphate, deoxyguanosine triphosphate, deoxycytodine triphosphate and thymidine triphosphate.

The phrase "capture reagent" as used herein is a solid phase that has been attached or coupled to a specific binding member. Coupling chemistries for synthesizing a capture reagent are well known and a matter of choice for one skilled in the art and may include any chemical means and/or physical means that does not destroy the specific binding property of the specific binding member or the solid nature of the solid phase.

The term "conjugate" as used herein means a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label.

The phrase "denaturation conditions" is defined generally as conditions which promote dissociation of double stranded nucleic acid to the single stranded form. These conditions can include high temperature and/or low ionic strength.

The phrase "hybridization conditions" is defined generally as conditions which promote nucleation, annealing and amplification of nucleic acid sequences. It is well known in the art that such annealing and hybridization is dependent in a rather predictable manner on several parameters, including temperature, ionic strength, sequence length and G:C content of the sequences. For any given set of sequences, melt temperature, or Tm, can be estimated by any of several known methods. Typically hybridization conditions include temperatures which are slightly below the melt temperature of a given set of nucleic acid sequences. Ionic strength or "salt" concentration also impacts the melt temperature, since small cations tend to stabilize the formation of duplexes by shielding the negative charge on the phosphodiester backbone. Typical salt concentrations depend on the nature and valence of the cation but are readily understood by those skilled in the art. Similarly, high G:C content and increased sequence lengths are also known to stabilize duplex formation because G:C pairings involve 3 hydrogen bonds where A:T pairs have just two, and because longer sequences have more hydrogen bonds holding the strands together. Thus, a high G:C content and longer sequence lengths impact what "hybridization conditions" will encompass. Based upon the above, determining the proper "hybridization conditions" for a particular set of nucleic acid sequences is well within the ordinary skill in the art.

The term "label" as used herein refers to a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirect labels are used for detection, they are typically used in combination with a conjugate as defined above.

The term "ligation" is a general term which includes any method of covalently attaching two appropriately situated nucleic acid sequences. The preferred method is enzymatic ligation. For purposes of this application, "ligation competent" refers to probe ends that are capable of being ligated. For known enzymatic ligases, ligation competency requires nucleic acid segments such that a 3' hydroxyl terminus is disposed adjacent to a 5' phosphorylated terminus.

The term "primer" as used herein means a nucleic acid sequence that hybridizes upstream from a probe sequence. The presence of a primer on a target sequence may facilitate degradation of a probe sequence hybridized to the same target strand. Also, as is known in the art, a primer may also prime synthesis of a sequence complementary to the target sequence to which the primer hybridizes. While the primer must be sufficiently complementary to the target sequence in order to hybridize, this does not mean that the entire primer sequence is complementary to the target sequence.

The term "probe" as used herein means a nucleic acid sequence that hybridizes to a target sequence downstream from a primer sequence and is degraded in a target sequence dependent manner which means that the probe is degraded only when it is hybridized to the target sequence. Probes according to the invention are labeled with at least two labels and at least one of the labels is a specific binding member. While the probe must be sufficiently complementary to the target sequence in order to hybridize, this does not mean that the entire probe sequence is complementary to the target sequence.

Probes and primers are nucleic acid sequences typically DNA or RNA. The length of the probes or primers is not critical but are usually 10 to about 100 nucleotides long, preferably from about 15–35, and have a defined base sequence suitable for the desired target. Such sequences can be from natural or synthetic sources and can routinely be synthesized using a variety of techniques currently available. For example, a sequence of DNA can be synthesized using conventional nucleotide phosphoramidite chemistry and the instruments available from Perkin Elmer/Applied Biosystems, Div., (Foster City, Calif.) or Perceptive Biosystems, Inc., (Framingham, Mass.). Similarly, and when desirable, the sequences can be labeled using methodologies well known in the art such as described in U.S. Pat. No. 5,464,746; 5,424,414; and 4,948,882 all of which are herein incorporated by reference. For convenience herein, the relationship between probes and primers hybridized to a target sequence are occasionally referred to as "upstream" or "downstream". When a primer and probe hybridize to distinct regions of the same linear target nucleic acid strand, and the 3' terminus of one primer points towards the 5' terminus of the probe, the former is called the "upstream" primer and the latter is called the "downstream" probe, regardless of whether the strand(s) possesses a "sense" direction for coding purposes.

The term "solid phase", as used herein, refers to any material which is insoluble, or can be made insoluble by a subsequent reaction. The solid phase can be chosen for its intrinsic ability to attract and immobilize a binding member to form a capture reagent. Alternatively, the solid phase can retain an additional receptor which has the ability to attract and immobilize a binding member to form a capture reagent. The additional receptor can include a charged substance that is oppositely charged with respect to a binding member or to a charged substance conjugated to a binding member. As yet another alternative, the receptor molecule can be any specific binding member which is immobilized upon (attached to) the solid phase and which has the ability to immobilize another binding member through a specific binding reaction. The receptor molecule enables the indirect binding of a binding member to a solid phase material before the performance of the assay or during the performance of the assay. The solid phase thus can be a latex, plastic, derivatized plastic, magnetic or non-magnetic metal, glass or silicon surface or surfaces of test tubes, microtiter wells, sheets, beads, microparticles, chips, and other configurations known to those of ordinary skill in the art. A preferred solid support is a microparticle.

The phrase "specific binding member" as used herein means a member of a binding pair, i.e., two different molecules where one of the molecules through, for example, chemical or physical means specifically binds to the other molecule. In addition to antigen and antibody binding pairs, other examples of specific binding pairs include, but are not intended to be limited to, avidin or streptavidin and biotin, a peptide or protein sequence and an antibody specific for the sequence or protein, complementary nucleic acid sequences, haptens and antibodies specific for the haptens such as carbazole and adamantane described in U.S. Pat. Nos. 5,424,414 and U.S. Pat. No. 5,464,746, respectively (the disclosures of these patents are incorporated herein by reference) and the like.

A "target sequence" or "target" as used herein means a nucleic acid sequence that is detected or both amplified and detected according to the method herein provided. Additionally, while the term target sequence is sometimes referred to as single stranded, those skilled in the art will recognize that the target sequence may actually be double stranded. Thus, in cases where the target is double stranded, probe and/or primer sequences can be hybridized to both strands of the target sequence according to the present invention.

The term "test sample" as used herein, means anything suspected of containing a target sequence. The test sample is or can be derived from any biological source, such as for example, blood, ocular lens fluid, cerebral spinal fluid, milk, ascites fluid, synovial fluid, peritoneal fluid, amniotic fluid, tissue, fermentation broths, cell cultures and the like. The test sample can be used (i) directly as obtained from the source or (ii) following a pre-treatment to modify the character of the sample. Thus, the test sample can be pre-treated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

The present method detects target sequences that may be present in a test sample using a probe having at least two labels wherein at least one of the labels is a specific binding member. Target sequences detected according to the present method can also be amplified according to nucleic acid amplification reaction principles. Given the labelling system, the probe itself is detectable using heterogeneous immunoassay techniques. In the presence of the target sequence and an appropriate primer, however, the probe is degraded and therefore no longer detectable. Hence, a decrease in the signal attributable to the probe indicates the presence of the target sequence. Accordingly, the invention is a detection method that is based upon the degradation of a probe hybridized to a target sequence, although amplification of the target can and preferably does result. Detecting a decrease in signal typically is an end-point type read, but it should be pointed out that the decrease in signal is coupled to the amplification and, as such, could be determined in a real time fashion after successive amplification cycles. Additionally, a more efficient detection is achieved in end-point read embodiments as compared to other detection schemes where products from an amplification reaction are separated and detected because such detection schemes rely upon events secondary from the amplification reaction itself (e.g. probe hybridizations with the amplification product) in order to achieve detection.

As is well known in the art, formation of the reaction mixture is accomplished under appropriate conditions where the probe and/or primer hybridize to the target sequence. Preferably, the probe is hybridized to the target sequence prior to or concomitantly with extension of the primer. Concentration adjustments can be made to insure that the probe is hybridized properly but preferably, the melt temperature (Tm) of the probe is greater than or equal to the Tm of the primer to insure preferred hybridization pattern. The precise concentrations of the primer and probe in the reaction mixture are not critical. Preferably, however, the probe is at or near a concentration where the concentration of the probe, per se, effects the signal. Specifically, above a certain concentration, different concentrations of the probe itself will yield approximately the same signal regardless of how much the concentration of the probe is increased (saturation point). On the other hand, below the saturation point, different concentrations of the probe yield an increase or decrease in signal. In terms of getting an efficient signal decrease upon degradation of the probe, it is preferred to have the concentration of the probe at or near the saturation point. However, the method is nevertheless efficacious at probe concentrations other than those close to the saturation point but the number of cycles and primer concentration can be adjusted to accommodate the increase or decrease in the probe concentration. Additionally, more sensitive detectable labels such as, for example, radioisotopes can be employed when less than optimal probe concentrations are employed.

Determining the saturation point for a particular probe or adjusting the number of cycles for use with a particular system can be determined empirically by, for example, detecting signals from various probe concentrations (or titrating the probe) or running reactions with various primer concentrations, as is commonly done in the art.

It will be understood, of course, that various combinations of primer and probe sequences can be employed as long as one primer and one probe that hybridize to the same strand of a target sequence are employed. For example, a primer and probe for both strands of a target sequence may be employed or, alternatively, a primer and probe for one strand of a target and only a primer for the other strand of the target can be employed.

Following formation of the reaction mixture and hybridization of the primer and probe to the target, if present, the probe is degraded. The probe , located downstream of the primer, can be degraded by an enzyme having 5'→3' exonuclease activity. According to one embodiment, an enzyme having both polymerase activity and 5'→3' exonuclease activity is used to first extend the primer sequence to thereby synthesize a copy of the target sequence and also degrade the probe when the extension product reaches the hybridized probe. The extension product can be dissociated from the target and the cycle repeated through, for example, thermal cycling. Thermal cycling is a well known procedure of alternating denaturation and hybridization conditions and is usually performed for 10 to 100 cycles. One preferred enzyme having both polymerase and 5'→3' exonuclease activity is a thermal stable polymerase such as Taq DNA polymerase, which is commercially available (e.g., Amplitaq™ from Perkin-Elmer, Norwalk, Conn.).

In a second embodiment, an enzyme having polymerase and 5'→3' exonuclease activity can extend the primer sequence and degrade the probe sequence to a pre-defined point in the probe by depriving the reaction mixture of at least one of the nucleotide triphosphates. Methods for stopping 5'→3' exonuclease activity in this manner have previously been described in U.S. Pat. No. 5,573,907 which is herein incorporated by reference. By stopping the 5'→3' exonuclease activity in this way, the remaining portion of the probe and extended primer are hybridized to the target in a ligation competent manner. Alternatively, amplification and degradation of the probe can be achieved using an enzyme having 5'→3' exonuclease activity that removes a non-complementary 5' end of the probe such that (i) a new 5' end is exposed and (ii) it is ligation competent with the primer. Many methods for ligating such sequences could be used but preferably, an enzyme having ligase activity is employed. Hence, a copy of the target sequence is generated. The copy number can be increased through cycling the reaction as described above.

As previously discussed, the probe can have two labels at least one of which is a specific binding member. In the presence of target, the specific binding member is separated from the other label by virtue of the degradative process. As a result, upon contacting the reaction mixture with a capture reagent, the binding member forms a complex with the capture reagent but the remaining part of the probe, including the other label, is not bound to the capture reagent. Accordingly, a decrease in signal from the second label will be detected, and such a decrease indicates the presence of the target sequence. On the other hand, if the target sequence is not present, the probe remains intact with both labels attached. In this latter case, there is no loss of signal due to the absence of the second label. As also discussed above, the second label may also comprise a specific binding member in which case, a conjugate is typically used to detect this label. It will be understood, of course, that wash steps can be employed after binding of the probe (or pieces thereof) to the capture reagent and/or after contacting the capture reagent with the conjugate.

"Multiplexing" or detecting 2, 3 or more target sequences according to the present method is also possible. In such cases, at least one additional primer/probe set is employed to detect the additional target sequences but as mentioned above, different configurations of primer/probe sets may be employed for each target sequence. For example, a primer and probe for each strand of the additional target(s) may be employed or a primer for each strand of the target sequence and only one probe may be employed. Additional target sequences detected according to multiplex embodiments may represent sequences from different analytes or in some cases, an internal control sequence. An internal control sequence typically is a nucleic acid having a sequence that is known at least in the regions where the primer and probe sequences hybridize. It can be used for purposes of determining whether or not an amplification reaction for an analyte target sequence was efficacious, or for purposes of competing with an analyte target sequence for primers in a quantitative amplification assay.

It will be understood, of course, that according to multiplexing embodiments, at least one target sequence is detected according to the present method but additional target sequences may be detected according to previously known amplification and detection methods. Thus, for example, an HIV target sequence in a reaction mixture can be detected according to previously known methods and a internal control sequence in the same reaction mixture can be detected according to the present method.

According to multiplex embodiments primer sequences may be distinct for all target sequences, the primers can be the same for all target sequences, or a combination thereof. Preferably, however, each target has a distinct probe sequence. Such probe sequences can have the same or different labeling systems but it is also preferable to have at least one different label for each probe to assist in differentiating the signals. In the event that the label that reacts with the capture reagent is distinct, probe sequences for various target sequences can be separated by immobilizing them (or their fragments) to different capture reagents using capture reagents comprising distinct specific binding members. Alternatively, the label that reacts with the capture reagent can be the same and different second labels can be employed to detect a loss in signal. For example, fluorophores having different emission spectra could be employed or enzymes having different substrates could be employed to detect multiple signal loss. It will be understood by those skilled in the art that because the index of a target sequences presence is a decrease in signal, it is preferred to have at least one baseline measurement to compare the loss of signal.

Figure 1B:
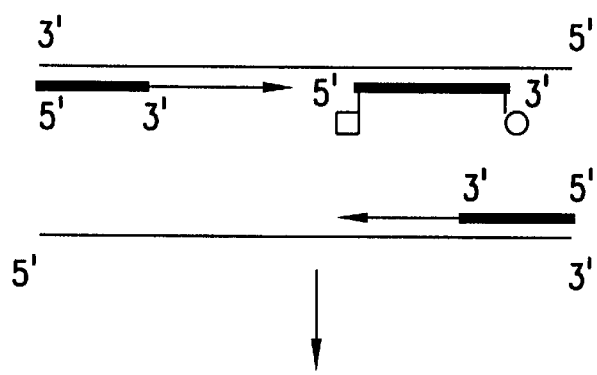
Figure 1C:
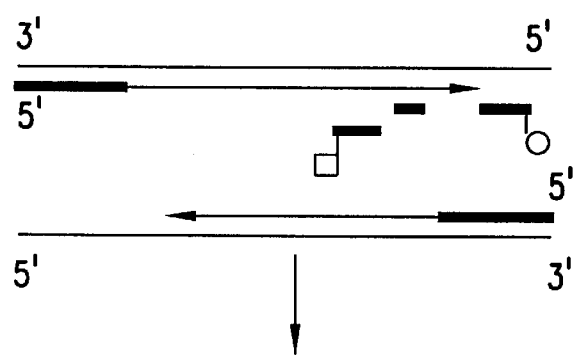
Figure 1D:
Figure 1E:
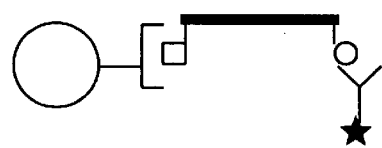

Embodiments of the invention will now be discussed in connection with the Figures. FIG. 1A shows a double stranded target sequence that is subsequently dissociated in FIG. 1B to allow (i) a primer and probe sequence to hybridize with one strand and (ii) a primer to hybridize to the other strand. FIG. 1B also shows the primers being extended and in FIG. 1C, primer extension reaches the probe at which point it becomes degraded to separate the labels depicted as a circle and square. The reaction mixture is then contacted with a capture reagent and as shown in FIG. 1D, the specific binding member/capture reagent complex is formed but the second label is not present and therefore not detectable thereby representing a decrease in signal. Conversely, if the target was not present and the reaction mixture was contacted with a capture reagent the intact probe could be detected by virtue of the presence of the second label as shown in FIG. 1E.

Figure 2A:
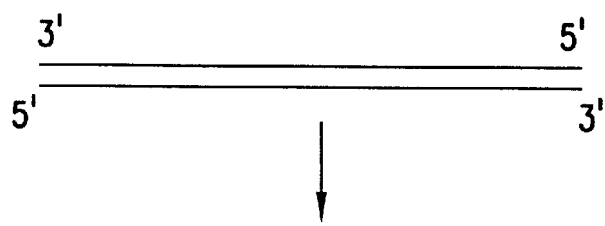
FIGS. 2(A)–(E) show another embodiment of the present invention
Figure 2B:
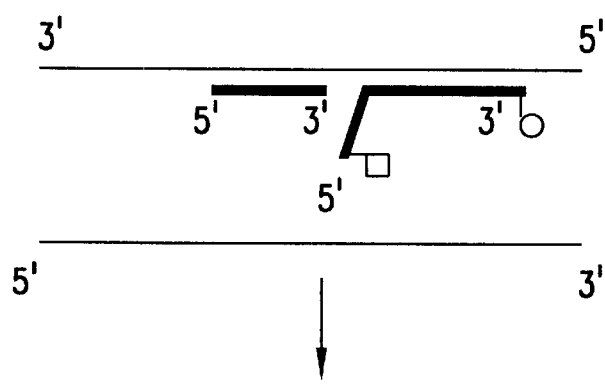
Figure 2C:
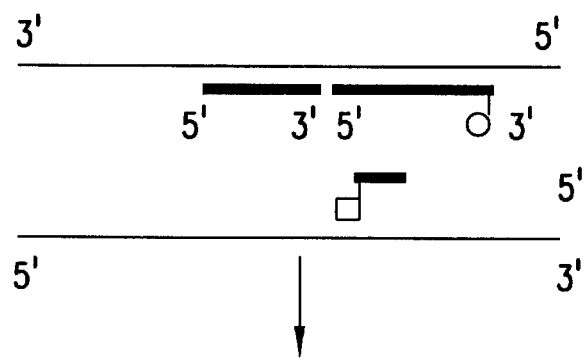
Figure 2D:
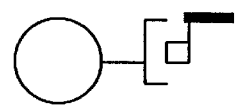
Figure 2E:
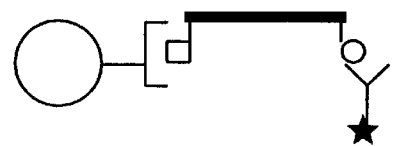

FIG. 2 shows another embodiment of the invention where a double stranded target sequence (FIG. 2A) is dissociated such that a primer and probe can hybridize to a strand of the target sequence as shown in FIG. 2B. Also shown by FIG. 2B is an imperfectly complementary probe where the 5' end of the probe does not hybridize to the target and is labeled, as represented by the square. FIG. 2C demonstrates the reaction mixture after an enzyme having 5'→3' exonuclease has acted to degrade the 5' noncomplementary region of the probe. At this point, ligase can act upon the primer and probe to ligate the adjacent primer and probe to thereby amplify the target sequence. Whether or not amplification occurs, the probe will be degraded as also shown in FIG. 2C to separate the two labels represented by the square and the circle. The reaction mixture from step 2C is then contacted with a capture reagent and, as shown in FIG. 2D, the specific binding member/capture reagent complex is formed but the second label is not present and therefore not detectable thereby representing a decrease in signal. Conversely, if the target was not present and the reaction mixture was contacted with a capture reagent, the intact probe could be detected by virtue of the presence of the second label as shown in FIG. 2E.

The following examples are provided to further illustrate the present invention and not intended to limit the invention.

EXAMPLES

The following examples demonstrate detection of HIV nucleic acid using the DNA oligomer primers and probes herein provided. These DNA primers and probes are identified as SEQUENCE ID NO. 2, SEQUENCE ID NO. 3, SEQUENCE ID NO. 4, SEQUENCE ID NO. 5, SEQUENCE ID NO. 6, SEQUENCE ID NO. 7, SEQUENCE ID NO. 8 and SEQUENCE ID NO. 9 and are specific for a region in the gag gene of HIV. The gag target sequence from HIV-1 (subtype B, strain SF-2) is designated herein as SEQ ID NO. 1.

In the following examples, SEQ ID NO. 2, SEQ ID NO. 3 and SEQ ID NO. 4 are used as amplification primers specific for the gag region of HIV and, where applicable, the internal control target. SEQ ID NO. 5, SEQ ID NO. 6 and SEQ ID NO. 7 are used as internal hybridization probes for the HIV gag region. SEQ ID NO. 8 and SEQ ID NO. 9 are used as internal control hybridization probes for the internal control target. The internal control target sequence is designated herein as SEQ ID NO. 10.

Example 1

Preparation of HIV Primers and Probes

A. HIV Primers/Internal Control Primers

Primers were designed to detect the HIV gag target sequence. These primers were SEQ ID NO. 2, SEQ ID NO. 3 and SEQ ID NO. 4. Primer sequences were synthesized using standard oligonucleotide synthesis methodology. The Internal Control target was an in-vitro transcribed RNA sequence that contained HIV/Internal Control primer binding sites but a different internal sequence for Internal Control probe binding.

B. HIV Probes

Probes were designed to hybridize with the HIV gag target sequence, in a region internal to both primers. These probes were SEQ ID NO. 5, SEQ ID NO. 6 and SEQ ID NO. 7. Probe sequences were synthesized using standard oligonucleotide synthesis methodology and haptenated with a carbazole at the 5' end and an adamantane at the 3' end using standard cyanoethyl phosphoramidite coupling chemistry as described in U.S. Pat. No. 5,464,746 (herein incorporated by reference).

C. Internal Control Probes

Internal control probes were designed to hybridize with an internal control target sequence, in a region internal to both primers. These probes were SEQ ID NO. 8 and SEQ ID NO. 9. Internal probe sequences were synthesized using standard oligonucleotide synthesis methodology and haptenated with a carbazole at the 5' end and a biotin at the 3' end using standard cyanoethyl phosphoramidite coupling chemistry as described in U.S. Pat. No. 5,464,746 (herein incorporated by reference).

Example 2

Titration of HIV and Internal Control Probes

Since signal from the HIV probe will decrease with increasing sample/target concentration, the optimal starting amount of probe needed which will be most sensitive to the presence of target DNA was determined. This was done by testing probe dilutions in the absence of target and looking for the point at which the test system no longer shows an increase in signal as more probe is added. This was done for HIV probe alone and for HIV probe(s) in combination with an Internal Control probe.

A. Titration of a Single HIV Probe

The HIV reverse strand probe (HIV RP), SEQ ID NO. 6 was diluted in 1×EZ Buffer (Perkin-Elmer, Foster City, Calif.) containing 2.5 mM manganese acetate and dilutions were tested in duplicate on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the probe. The enzyme substrate used was methyl-umbelliferyl phosphate (MUP), with the rate of conversion of MUP to MU measured and reported as counts/second/second (c/s/s).

Data from this experiment is presented in TABLE 1 and shows signal detection beginning to plateau at approximately 17 nM of probe.

TABLE 1

| HIV Probe Concentration (nM) | Mean LCx ® rate |
| --- | --- |
| 0 | 8.2 |
| 0.0525 | 12.3 |
| 0.0933 | 17.4 |
| 0.166 | 24.1 |
| 0.296 | 37.8 |
| 0.525 | 62.8 |

TABLE 1-continued

| HIV Probe Concentration (nM) | Mean LCx ® rate |
|---|---|
| 0.933 | 105.2 |
| 1.66 | 171.2 |
| 2.96 | 266.6 |
| 5.25 | 427.7 |
| 16.6 | 800.4 |
| 52.5 | 1071.6 |

B. Independent and Simultaneous Titration of HIV and Internal Control Probes

To determine how the simultaneous presence of both the HIV and Internal Control probes might affect the signal for each, they were titrated in separate reactions, then together in the same reaction. Two HIV probes, HIV forward strand probe (HIV FP; SEQ ID NO. 5) and HIV RP (SEQ ID NO. 6), were used with Internal Control probes, SEQ ID NO. 8 (IC FP) and SEQ ID NO. 9 (IC RP). All probes were tested in separate reactions, then each Internal Control probe was tested together in the same reaction with each HIV probe. All probes were diluted to concentrations of 30, 25, 20, 15, 10, 5, 1, 0.5, 0.25 and 0.125 nM in 1×EZ Buffer (Perkin-Elmer, Foster City, Calif.) containing 2.5 mM manganese acetate. Testing was performed on the Abbott LCx® system as in Example 2.A. using the anti-adamantane antibody/alkaline phosphatase conjugate to detect the HIV probe, or an anti-biotin/alkaline phosphatase conjugate to detect the Internal Control probe. Reaction mixtures were divided in two with one set tested using one conjugate and the other set tested using the other conjugate.

TABLE 2

| Probe Conc. (nM) | LCx ® Rate (c/s/s) | | |
|---|---|---|---|
| | HIV FP | HIV FP and IC FP | HIV FP and IC RP |
| 30 | 1594.9 | 1195.5 | 1029.5 |
| 25 | 1519.4 | 1166.4 | 1052.6 |
| 20 | 1510.8 | 1162.7 | 1166.1 |
| 15 | 1408.9 | 1052.9 | 1143.5 |
| 10 | 1119.6 | 956.9 | 1025.6 |
| 5 | 842.9 | 746.9 | 639.2 |
| 1 | 269.5 | 127.3 | 276.0 |
| 0.5 | 163.9 | 156.4 | 195.7 |
| 0.25 | 51.7 | 90.4 | 117.4 |
| 0.125 | 83.0 | 46.5 | 42.2 |
| | HIV RP | HIV RP and IC FP | HIV RP and IC RP |
| 30 | 1389.1 | 1140.7 | 711.5 |
| 25 | 1307.3 | 1067.1 | 706.1 |
| 20 | 1230.5 | 1052.4 | 784.0 |
| 15 | 1126.2 | 1048.0 | 744.1 |
| 10 | 934.1 | 871.7 | 661.6 |
| 5 | 664.5 | 655.7 | 471.6 |
| 1 | 190.7 | 207.8 | 157.9 |
| 0.5 | 120.2 | 128.0 | 87.6 |
| 0.25 | 60.4 | 63.9 | 53.6 |
| 0.125 | 34.7 | 38.1 | 35.1 |
| | IC FP | IC FP and HIV FP | IC FP and HIV RP |
| 30 | 1430.3 | 1295.7 | 1479.5 |
| 25 | 1331.8 | 1264.9 | 1386.2 |
| 20 | 1332.4 | 1210.9 | 1392.8 |
| 15 | 1288.8 | 1188.1 | 1386.6 |
| 10 | 1171.0 | 1097.3 | 1301.3 |
| 5 | 935.9 | 918.2 | 1087.5 |
| 1 | 303.2 | 140.8 | 392.5 |
| 0.5 | 175.8 | 200.4 | 233.9 |

TABLE 2-continued

| Probe Conc. (nM) | LCx ® Rate (c/s/s) | | |
|---|---|---|---|
| 0.25 | 93.8 | 107.0 | 118.5 |
| 0.125 | 49.2 | 51.3 | 61.3 |
| | IC RP | IC RP and HIV FP | IC RP and HIV RP |
| 30 | 1487.0 | 1456.3 | 1483.3 |
| 25 | 1564.4 | 1459.1 | 1415.4 |
| 20 | 1418.7 | 1343.1 | 1363.9 |
| 15 | 1320.2 | 1250.9 | 1224.7 |
| 10 | 1174.4 | 1133.6 | 1132.4 |
| 5 | 866.1 | 710.6 | 613.2 |
| 1 | 258.0 | 242.5 | 248.5 |
| 0.5 | 128.6 | 116.4 | 117.5 |
| 0.25 | 67.9 | 62.9 | 73.4 |
| 0.125 | 36.0 | 35.3 | 33.3 |

The results in Table 2 indicate that the signals from each probe begin to plateau at a probe concentration around 10 nM. The signal from the Internal Control probes does not appear to be significantly affected by the presence of either HIV probe, but the signal from the HIV strobes is affected by the addition of an Internal Control probe. HIV probe signals decreased 30 to 50% when an Internal Control probe was also present. The concentrations of the probes are adjusted or chosen such that the signals from each probe was below the saturation point.

Example 3

Detection of HIV

HIV RNA was isolated from a known quantity of virions (Advanced Biotechnologies Inc., Columbia, Md.) using the Ultraspec RNA Isolation System (Biotecx, Houston, Tex.), extracted with chloroform/isopropanol and precipitated with ethanol. The pellet was resuspended in RNase-free water (5prime3prime, Boulder, Colo.). Ten-fold dilutions of this HIV RNA were then prepared at concentrations of $10^5$ to $10^1$ RNA molecules/25 $\mu$l using a diluent containing 20 ng/$\mu$l of ribosomal RNA (rRNA; Boehringer-Mannheim, Indianapolis, Ind).

Dilutions of the HIV RNA were reverse transcribed, PCR amplified and detected using SEQ ID NOs. 2 and 3 as primers with the two different HIV probes, HIV FP (SEQ ID NO. 7) and HIV RP (SEQ ID NO. 6) used individually as probes in separate reactions, or simultaneously at 2 different concentrations. RT-PCR was performed using IX EZ Buffer, 2.5 mM manganese acetate, dNTPs (dATP, dGTP, dTTP and dCTP) present at a final concentration of 0.15 mM each, and recombinant *Thermus thermophilus* polymerase at a concentration of 5 units/reaction.

Primers were used at a concentration of 250 nM each, and probes were used at a concentration of 16.6 nM each when used in separate reactions, and at both 16.6 nM or 8.3 nM each when used simultaneously. The ten-fold dilutions of HIV RNA in a sample volume of 25 $\mu$l were added to 175 $\mu$l containing the above mixture for a total reaction volume of 0.2 ml. The negative control was composed of 500 ng of rRNA/reaction.

Reaction mixtures were reverse transcribed and amplified in a Perkin-Elmer 480 Thermal Cycler. Reaction mixtures were first incubated at 62° C. for 30 minutes to reverse transcribe the RNA, followed by 1 minute at 94° C. PCR amplification was performed using 35 or 45 cycles of 94° C. for 30 seconds followed by 62° C. for 2 minutes. After the reaction mixtures were thermal cycled, the mixtures were maintained at 97° C. for 5 minutes then the temperature was decreased to 62° C. over 20 minutes for PCR product reannealing. The temperature was then lowered to 4° C. and samples were held at 4° C. until detection of reaction products. Reaction products were detected on the Abbott LCx® system as described in Example 2.A.

Data from this experiment is presented in Table 3 and shows detection of HIV RNA to at least 100 molecules/reaction with all probes using 35 cycles of PCR. When PCR is increased to 45 cycles, the sensitivity of detection of HIV RNA increases to at least 10 molecules/reaction with all probes.

TABLE 3

| HIV RNA (molecules) | HIV RP (16.6 nM ea.) | HIV FP (16.6 nM ea.) | Both Probes (8.3 nM ea.) | Both Probes (16.6 nM ea.) |
|---|---|---|---|---|
| LCx ® Rate (c/s/s) with 35 cycles | | | | |
| 0 | 1103.1 | 1213.1 | 1174.0 | 1353.3 |
| $10^1$ | 821.5 | 1149.3 | 1054.6 | 1300.3 |
| $10^2$ | 871.1 | 1018.3 | 878.7 | 1125.8 |
| $10^3$ | 545.9 | 768.2 | 631.5 | 782.1 |
| $10^4$ | 358.3 | 579.5 | 439.6 | 546.3 |
| $10^5$ | 185.8 | 431.9 | 273.8 | 397.9 |
| LCx ® Rate (c/s/s) with 45 cycles | | | | |
| 0 | 1050.9 | 1169.6 | 1089.6 | 1243.9 |
| $10^1$ | 536.8 | 1156.0 | 871.9 | 1107.7 |
| $10^2$ | 504.8 | 832.8 | 585.7 | 721.7 |
| $10^3$ | 358.8 | 580.1 | 365.5 | 458.9 |
| $10^4$ | 209.5 | 407.7 | 277.5 | 391.5 |
| $10^5$ | 111.3 | 315.5 | 176.5 | 257.5 |

Example 4

Detection of HIV with an Internal Control

The HIV sample used in the following experiment was a 675 nucleotide transcript from the gag region of HIV. The HIV gag region sequence was inserted into a bacterial plasmid vector and the bacteria were cultured. The HIV RNA gag transcript was prepared by first linearizing the plasmid DNA using the restriction enzyme EcoRI, then extracting the DNA with phenol/chloroform followed by ethanol precipitation. The amount of DNA present was quantitated spectrophotometiically using absorbance at 260 nm. The DNA was then transcribed using the Ambion mMessage mMachine Kit (Austin, Tex.) following the manufacturer's directions. Next, the RNA transcript was extracted using phenol/chloroform and run through a Select I size exclusion gel column (5prime3prime). The HIV RNA gag transcript was quantitated by spectrophotometric means and serially diluted from $5 \times 10^7$ to $5 \times 10^1$ copies/12.5 µl.

Dilutions of the HIV gag transcript, along with the Internal Control target sequence (SEQ ID NO. 10) transcript (prepared similarly to the above HIV transcript) were reverse transcribed, PCR amplified and detected using SEQ ID NOs. 3 and 4 as primers with the HIV probe, HIV FP (SEQ ID NO. 5), and the Internal Control probe, IC RP (SEQ ID NO. 8). RT-PCR was performed using 1×EZ Buffer, 2.5 mM manganese acetate, dNTPs (dATP, dGTP, dTTP and dCTP) present at a final concentration of 0.15 mM each, and recombinant *Thermus thermophilus* polymerase at a concentration of 5 units/reaction. Primers were used at a concentration of 250 nM each, probes were used at a concentration of 5 nM each, and the Internal Control transcript was present at a concentration of $5 \times 10^4$ copies/reaction. Duplicates of the ten-fold dilutions of HIV gag transcript in a sample volume of 12.5 µl were added to the above mixture in a total reaction volume of 0.2 ml. The negative control was composed of 500 ng of rRNA/reaction.

Reaction mixtures were reverse transcribed and amplified in a Perkin-Elmer 480 Thermal Cycler. Reaction mixtures were first incubated at 62° C. for 30 minutes to reverse transcribe the RNA, followed by 1 minute at 94° C. PCR amplification was performed using 45 cycles at 94° C. for 30 seconds followed by 62° C. for 2 minutes. After the reaction mixtures were thermal cycled, the temperature was lowered to 4° C. and samples were held at 4° C. until detection of reaction products.

Reaction products were detected on the Abbott LCx® system. A suspension of anti-carbazole antibody coated microparticles, a strepavidin/β-galactosidase conjugate and an anti-adamantane antibody/alkaline phosphatase conjugate were used in conjunction with the LCx® to capture and detect the probes. The enzyme substrates used were methylumbelliferyl phosphate (MUP) and 4-methylumbelliferyl β-D-galactosidase (MUG), with the rate of conversion of substrate to product measured and reported as counts/second/second (c/s/s). The rate of conversion of MUP to product represented the signal from the HIV probe and the rate of conversion of MUG to product represented the signal from the Internal Control probe.

In this experiment the Internal Control transcript competes with the sample HIV gag transcript for primer binding. Thus, in samples with high amounts of HIV gag transcript, most of the primers will bind to the HIV transcript, resulting in increased HIV probe digestion with decreased HIV probe signal and decreased Internal Control probe digestion with increased Internal Control probe signal. Conversely, in samples with low amounts (or no) HIV transcript, most of the primers will bind to the Internal Control transcript, resulting in increased Internal Control probe digestion thereby decreasing the signal from the Internal Control probe, and decreased HIV probe digestion giving increased signal from the HIV probe.

Data from this experiment is presented in Table 4 and demonstrates the above.

TABLE 4

| HIV gag Transcript | Mean LCx ® Rate (c/s/s) | |
|---|---|---|
| (copies) | Internal Control Probe | HIV Probe |
| 0 | 111.6 | 668.5 |
| $5 \times 10^1$ | 107.4 | 555.5 |
| $5 \times 10^2$ | 124.4* | 361.4 |
| $5 \times 10^3$ | 145.6 | 94.2 |
| $5 \times 10^4$ | 223.3 | 37.3 |
| $5 \times 10^5$ | 280.4 | 24.4 |
| $5 \times 10^6$ | 412.3 | 19.5 |
| $5 \times 10^7$ | 597.5 | 20.2 |

*value of single replicate, other value of 467.5 considered aberrant

While the invention has been described in detail and with reference to specific embodiments, it will be apparent to one skilled in the art that various changes and modifications may be made to such embodiments without departing from the spirit and scope of the invention.

What is claimed is:

1. A method for detecting the presence of a target in a test sample comprising the steps of:
   (a) forming a reaction mixture comprising the test sample, a primer, a probe and amplification reagents wherein
      (i) the probe has a first and second label wherein the first label comprises a first specific binding member, and
      (ii) the primer and probe hybridize to the target such that the probe is downstream from the primer;
   (b) hybridizing the primer and probe to the target sequence and degrading the hybridized probe in a target dependent manner to separate the first and second labels;
   (c) contacting the reaction mixture with a capture reagent to form a first specific-binding-member/capture reagent complex;
   (d) detecting the second label associated with the first specific-binding-member/capture reagent complex, wherein a loss of signal indicates the presence of the target sequence;
   wherein said amplification reagents comprise an enzyme having 5'→3' exonuclease activity capable of degrading the hybridized probe only when the probe is hybridized to the target sequence.

2. The method of claim 1 wherein the primer and probe have a melt temperature and the melt temperature of the probe is greater than or equal to the melt temperature of the primer.

3. The method of claim 1 wherein the second label comprises a second specific binding member.

4. The method of claim 3 further comprising the step of contacting the first specific-binding-member/capture reagent complex with a conjugate prior to detecting the second label.

5. The method of claim 4 further comprising a wash step after forming the first specific-binding-member/capture reagent complex and prior to contacting with the conjugate and further comprising a wash step after contacting the first specific-binding-member/capture reagent complex with the conjugate but prior to detecting the second label.

6. The process of claim 1 wherein the amplification reagents further comprise an enzyme having polymerase activity.

7. The process of claim 1 wherein the amplification reagents further comprise an enzyme having ligase activity.

8. The method of claim 1 further comprising cycling steps (a) and (b) 10 to 100 times prior to steps (c) and (d).

9. The method of claim 1 wherein the reaction mixture further includes a second primer that hybridizes to a second strand of the target sequence.

10. The method of claim 1 wherein the target sequence is an internal control sequence and the method further comprises detecting an additional target sequence in the reaction mixture.

11. The method of claim 1 wherein the target sequence is from an analyte and the method further comprises detecting an internal control sequence.

12. The method of claim 1 wherein said reaction mixture further comprises a second target sequence and a second primer and probe wherein
   (i) the second probe has a third and fourth label wherein the third label is distinct from the second label and the fourth label comprises a specific binding member, and
   (ii) the second primer and probe hybridize to the second target such that the second probe is downstream from the second primer.

13. The method of claim 12 wherein the second target sequence is an internal control sequence.

14. The method of claim 13 wherein the method is a quantitative method for detecting the amount of the target sequence.

* * * * *